(12) United States Patent
Ajami et al.

(10) Patent No.: US 6,693,198 B2
(45) Date of Patent: Feb. 17, 2004

(54) AMONAFIDE SALTS

(75) Inventors: Alfred M. Ajami, Brookline, MA (US); David O. Barlow, Byfield, MA (US)

(73) Assignee: Xanthus Life Sciences, Inc., Montreal (CA)

( * ) Notice: Subject to any disclaimer, the term of this patent is extended or adjusted under 35 U.S.C. 154(b) by 13 days.

(21) Appl. No.: 10/128,129

(22) Filed: Apr. 22, 2002

(65) Prior Publication Data

US 2003/0203932 A1 Oct. 30, 2003

(51) Int. Cl.[7] ............... C07D 22/14; A61K 31/473; A61P 35/00

(52) U.S. Cl. ............... 546/100; 546/99; 544/60; 544/126; 544/361; 514/296; 514/232.8; 514/228.2; 514/253.03

(58) Field of Search ............... 546/99, 100; 514/296, 514/232.8, 228.2, 253.02; 544/126, 60, 361

(56) References Cited

U.S. PATENT DOCUMENTS

| | | | |
|---|---|---|---|
| 4,204,063 A | | 5/1980 | Brana et al. |
| 4,614,820 A | * | 9/1986 | Zee-Cheng et al. ......... 544/126 |
| 4,665,071 A | | 5/1987 | Zee-Cheng et al. |
| 5,183,821 A | | 2/1993 | Brana et al. |
| 5,420,137 A | | 5/1995 | Brana et al. |
| 2002/0025916 A1 | | 2/2002 | Brown |

FOREIGN PATENT DOCUMENTS

| | | |
|---|---|---|
| DE | 2323555 | 8/1974 |
| ES | 533.542 | 9/1983 |
| WO | WO 01/78705 A2 | 10/2001 |

OTHER PUBLICATIONS

Braña, Miguel Fernández, and Sanz, Antonio Martinez, "Synthesis and Cytostatic Activity of Benz(de)iso-quinolin–1, 3–Diones. Structure–Activity Relationships," *Eur. J. Med. Chem.–Chimica Therapeutica* 16(3): 207–202 (1981).
Braña, F.M., "Mitonafide and Amonafide," *Ars. Pharmaceutica* 36(3): 377–415 (1995).

* cited by examiner

*Primary Examiner*—Evelyn Mei Huang
(74) *Attorney, Agent, or Firm*—Hamilton, Brook, Smith & Reynolds, P.C.

(57) ABSTRACT

Disclosed is a salt of amonafide or amonafide analogs represented Structural Formula (I):

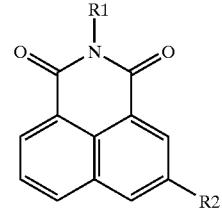

R1 is —$(CH_2)_n N^+HR3R4\ X^-$ or R1 is —$(CH_2)_n N^+ HR3R4\ X^-$ or —$(CH_2)_n NR3R4$ when R2 is —$N^+HR6R7$. R2 is —OR5, halogen, —NR6R7, —$N^+HR6R7\ X^-$ sulphonic acid, nitro, —NR5COOR5, —NR5COR5 or —OCOR5; R3 and R4 are independently H, C1–C4 alkyl group or, taken together with the nitrogen atom to which they are bonded, a non-aromatic nitrogen-containing heterocyclic group; each R5 is independently —H or a C1–C4 alkyl group; R6 and R7 are independently H, C1–C4 alkyl group or, taken together with the nitrogen atom to which they are bonded, a non-aromatic nitrogen-containing heterocyclic group; n is an integer from 0–3; and $X^-$ is the carboxylate anion of an organic carboxylic acid compound. Also disclosed are methods of preparing certain compounds represented by Structural Formula (I).

27 Claims, 1 Drawing Sheet

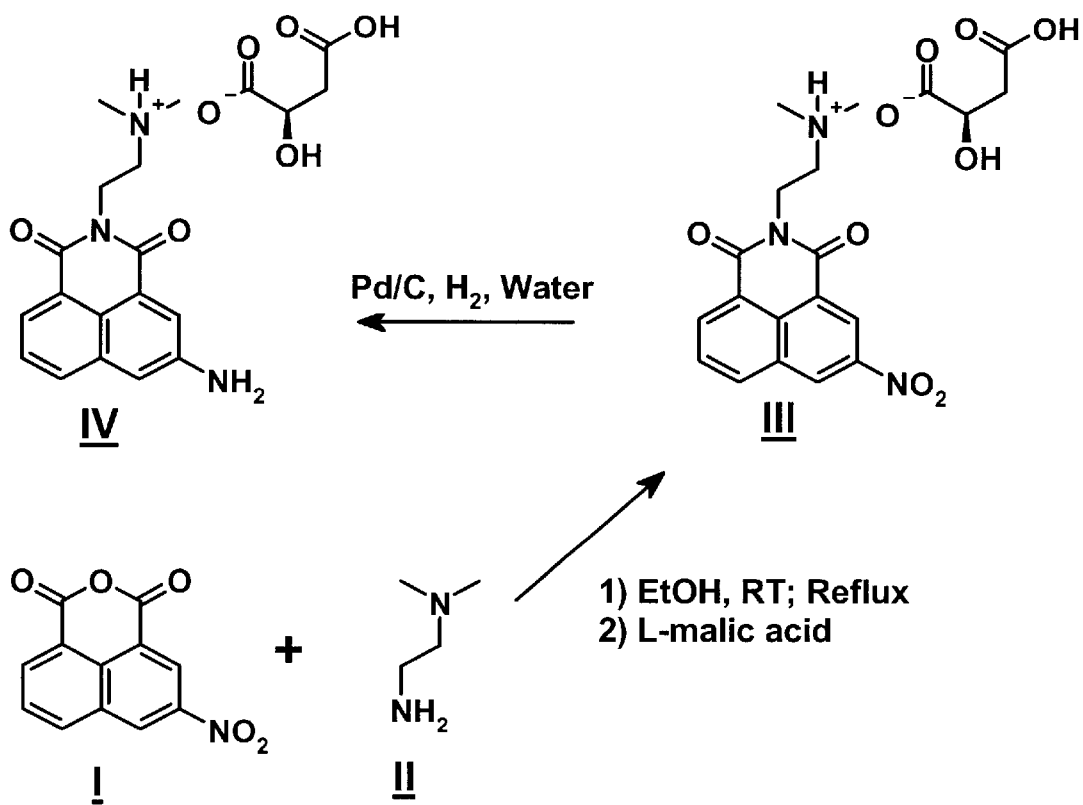
The Figure

AMONAFIDE SALTS

BACKGROUND OF THE INVENTION

Traditional pharmaceutical process technology for manipulating the physical properties and water solubility of these important anti-cancer drug moieties has been to render them water soluble with strong mineral acids. Salt formation is reserved as the final step in the synthesis, as described by Brana and associates (U.S. Pat. No. 5,420,137; 1995) more as an after thought for formulation purposes than as an integral or even strategic component, of the reaction synthesis. Such mono and divalent mineral acid salts retain hygroscopicity, and the divalent species, which form hydrates, have also been found to be incompatible with many pharmaceutical auxiliaries required for preparing sterile injectables, tablets or gelatin capsules.

In contradistinction to the prior art and accepted practice, we have found that the early incorporation of organic acids into the synthetic elaboration of amonafide and its aminoalkyl analogs moieties permits more rapid isolation and purification of intermediates, higher concentrations of reactants during the synthetic process, and more desirable properties, such as bulk density, flocculence and compressibility.

Furthermore, the resulting organic salts show higher solubilities in water as well as in osmotically balanced electrolyte solutions, which otherwise would be incompatible via common ion effects with inorganic, mineral acid salts such as the hydrochlorides and methylsulfonates used routinely heretofore. Moreover, organic acid salts of the present invention retain a higher degree of amphiphilic compatibility both with protic and aprotic solvents of varying polarity, thereby affording a broader range of crystallizing conditions for purposes of purification and isolation than would be afforded by the corresponding mineral acid salts.

Examination of the process chemistry for amonafide readily illustrates the shortcomings of the prior art and the adverse properties of the resulting mineral salts, which have been circumvented by the present invention. Among the synthetic approaches described in the patent and professional literature, the common denominator requires acylation of 1-amino-2,2-N,N-dimethylamino ethylene diamine, or its similarly substituted homologs, with a polycyclic, substituted aryl anhydride as shown in The Figure. Thus for amonafide, in accordance with the method of Brana and Sanz (Eur. J. Med. Chem 16:207, 1981) compounds I and II in The Figure are combined in ethanol to afford a precipitate of mitonafide, which must then be recrystallized multiple times from a larger volume of ethanol to be freed of tarry-black or brown by-products.

While the acylation may be conducted at a concentration of 1 gram of precursor anhydride in 25 ml of solvent, recrystallization of mitonafide requires three recrystallizations at a concentration of 1 gr in 75 ml to afford light cream colored material, free of tarry substances and exhibiting a constant melting. Although the initial yields according this process range within 60–80 percent, subsequent purification reduces the net yield to 30% of material with sufficient purity for subsequent conversion into a pharmaceutically acceptable end-product.

These isolation and purification conditions also apply to the synthesis of mitonafide analogs in toluene followed by precipitation with excess gaseous hydrochloric acid, as described by Zee-Cheng and Cheng (U.S. Pat. No. 4,665,071; 1987). The mitonafide hydrochloride, of unspecified stoichiometry and hydration, obtained by this reaction is a reddish brown precipitate, containing 12% by weight of tar with no differential solubility between water and alcohol, again requiring multiple recrystallizations to afford a hydrochloride salt material of suitable quality for pharmaceutical use.

In the present invention, as shown in The Figure, it has now been found that the isolation of the mitonafide moiety (III) from the ethanolic reaction mixture is facilitated by admixture and complete dissolution of a suitable organic carboxylic acid compound, which upon cooling affords a near colorless adduct upon crystallization from a mother liquor which retains the preponderance of colored impurities which might otherwise have co-crystallized as in the case of the prior art. In contrast to the synthetic approach of Brana and associates (Eur. J. Med. Chem 16:207, 1981; U.S. Pat. No. 4,204,063; 1980), described hereinabove, the mitonafide is obtained directly as an organic salt, in the first step of the synthesis for the target amonafide compound, rather than post facto in accordance with the alternate teachings as in U.S. Pat. No. 5,420,137 (1995) relating to the monohydrochloride or monomethylsulfate salts of amonafide obtained by controlled titration of amonafide itself at the end of the reaction sequence.

Those skilled in the art will also recognize that salt formation of mitonafide as an isolation step as taught by U.S. Pat. No. 4,665,071 (1987) cannot be construed as an obvious precedent for the instant invention insofar as organic acids, which are the salt forming reagents in this invention are known to be insoluble in toluene, and similar non-polar solvents, even at reflux. Unlike gaseous HCl used in accordance with the prior art on mitonafide salt isolation, the organic acids of this invention are solids which can be metered with accuracy so as to achieve a precise titration stoichiometry, an elusive objective when the dispensing of gaseous acids is called for as the prevailing alternative.

The novelty of the invention described here, when contrasted to prior art, is further affirmed by the unexpected finding concerning the catalytic hydrogenolysis of the nitro substituents in the mitonafide structural skeleton.

In the specific prior art on the formation of amonafide salts, congeneric with Stucture IV in The Figure, Brana and associates (U.S. Pat. No. 5,420,137; 1995) fail to describe the properties of the precursor mitonafide nor do they describe the method of hydrogenation to the resulting amonafide free base. However, in prior disclosures (Spanish Patent 533,542; 1983) on a method for the industrial production specifically of amonafide, these same authors indicate that nitro reduction of the precursor mitonafide free base is effected with 10% palladium-on-carbon (Pd/C) via transfer hydrogenation in the presence of excess hydrazine under refluxing ethanolic conditions. This procedure is also summarized as the preferred approach in the chemical review literature by the same authors (Ars Pharmaceutica 36:377–415, 1995).

Those skilled in the art would recognize that such an approach could not be practiced if the mitonafide precursor were composed of a pre-formed acid salt. Under such circumstances, one might reasonably expect that the hydrazine donor reagent would be neutralized by ion exchange and become unavailable as a substrate for diimide formation, which is the active reducing species catalyzed by Pd/C. In effect, any followers of the teachings of Brana and associates would have contemplated only the use of free-base precursors rather than resorting to the less obvious alternative, namely direct reduction of a mitonafide salt as taught in this patent.

Within the larger scope of organic functional group transformations, those skilled in the art will recognize that the catalytic hydrogenation of aryl nitro compounds to the corresponding substituted anilines is usually practiced in ethanol, mixtures of ethanol and water, or in the so called universal solvents (e.g. dimethyformamide and dimethylacetamide) which are resistant to hydrogenation. Respected, classical monographs on the subject by P. N. Rylander (Catalytic Hydrogenation in Organic Synthesis, New York: Academic Press, 1979) and M. Freifelder (Practical Catalytic Hydrogenation, New York: Wiley, 1971) acknowledge that the solubility of aryl nitro compounds in general precludes use of water as the hydrogenation medium.

These experts also indicate that the preferred source of protons to effect suppression of the imine and oxime by-products of incomplete hydrogenation is achieved by admixture of the substrate with hydrochloric acid. Even in the presence of mineral acids, hydrogenations in water are poorly documented and considered idiosyncratic in both the traditional and current hydrogenation laboratory and industrial practice. Use of organic acids, such as acetic acid or formic acid, has been described, but with the caveat that dehydrative acylation will occur, thus affording the corresponding N-acyl aryl-amines as yield-lowering contaminants.

Thus, in the context of this invention, neither the specific literature on amonafide synthesis nor on methods of hydrogenation can be cited as precedent for the non-obvious chemical manipulations which were found to be advantageous here. First, the use of organic carboxylic acid compounds to effect purification and isolation of mitonafide and its analogs has not been described heretofore. Second, application of organic carboxylic acid salts of mitonafide and its analogs as direct precursors for catalytic hydrogenation has not be considered or promulgated as an effective practice. Third, the high degree of water solubility of these organic salts, itself an unexpected phenomenon, coupled with the reluctance among experts to recommend catalytic hydrogenations in water as the sole solvent, would have precluded exploration of the novel approach presented here.

Beyond these issues which demonstrate non-obviousness, there exist further practical advantages to the use of organic carboxylic acid compounds, and especially their preferred analogs, the organic carboxylic diacid compounds, in the context of this invention. The resulting aralkyl naphthalimide salts show water solubilites as high as 1:1 by proportional admixture in contrast to the mono or divalent salts of hydrochloric, methanesulfonic, or of other mineral acids, whose solubilities fall below 10% by weight. Bulk processing is facilitated for purposes of industrial synthesis, filtration, purification, and dispensing of dosage units prior to sterile filtration and lyophilization.

In dry form, these organic carboxylic acid salts show higher bulk density, porosity and compaction than their analogs mineral acid salts, while presenting lower hygroscopicity. Thus, they are more suitable for processing by direct pressing, rather than solely by granulation or agglomeration.

In terms of biological burden, the organic carboxylate anions present no electrolyte load, unlike the mineral acid anions, and are biodegradable through normal cellular pathways of intermediary metabolism. In either the case of inorganic or organic acid anions, it is a matter of record that these species provide charge balance, solubility, mechanical, adsorptive or absorptive properties to the drug moiety to which they are attached. However, it is known throughout the practice of medicinal and pharmaceutical chemistry that the salt form per se will not affect the pharmacological activity, which in the case of the polycyclic aryl and aralkylamine containing intercalator drugs is their antitumor action.

For example, in reviewing the current pharamacopoeia, the intercalator drug amentantrone is known to be equally active as the free base, hydrochloride, monoacetate and diacetate, the difference in the salt form being their bulk formulation properties. Its analog, NSC-639366, on the other hand is being developed preclinically as the fumarate salt, in preference to the hydrochloride or acetate. In the case of asulacrine, the preferred salt form is the isethionate. For crisnatol and exatecan, it is the mesylate which is pharmaceutically most suitable. Many other drug classes, with diverse modes of action, have been developed as salts of organic acids. For example, the L-malate salts of clebopride, an antinausea medication, of almotriptan, an antimigraine medication, and of pizotifen, an antihistamine, have exhibited enhanced solubility without alteration of their respective medicinal properties.

SUMMARY OF THE INVENTION

One embodiment of the present invention is a compound represented by Structural Formula (I):

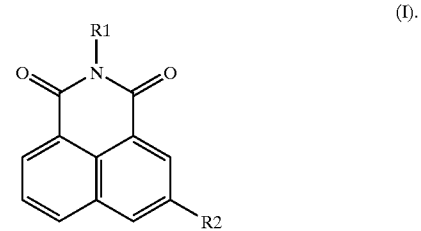

R1 is —$(CH_2)_n N^+ HR3R4$ $X^-$ or R1 is —$(CH_2)_n N^+ HR3R4$ $X^-$ or —$(CH_2)_n NR3R4$ when R2 is —$N^+ HR6R7$.

R2 is —OR5, halogen, —NR6R7, —$N^+ HR6R7$ sulphonic acid, nitro, —NR5COOR5, —NR5COR5 or —OCOR5.

R3 and R4 are independently H, C1–C4 alkyl group or, taken together with the nitrogen atom to which they are bonded, a non-aromatic nitrogen-containing heterocyclic group.

Each R5 is independently —H or a C1–C4 alkyl group.

R6 and R7 are independently H, a C1–C4 alkyl group or, taken together with the nitrogen atom to which they are bonded, a non-aromatic nitrogen-containing heterocyclic group.

n is an integer from 0–3.

$X^-$ is the carboxylate anion of an organic carboxylic acid compound. Examples of suitable organic carboxylic acids are provided below.

Another embodiment of the present invention is a method of preparing a product compound represented by Structural Formula (II):

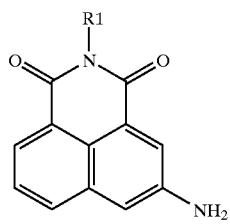
(II).

The product compound is prepared by hydrogenating in water a starting compound represented by Structural Formula (III):

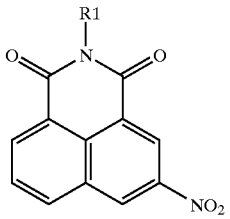
(III).

R1 in Structural Formulas (II) and (III) is —(CH$_2$)$_n$N$^+$HR3R4 X$^-$ and n, R3, R4 and X$^-$ are as described in Structural Formula (I). The hydrogenation can be carried out without admixture of alcoholic solvents, mineral acids, organic acids or hydrazine.

Another embodiment of the present invention is a pharmaceutical composition comprising a pharmaceutically acceptable carrier or diluent and a compound of the present invention.

Another embodiment of the present invention is a method of treating a subject with cancer. The method comprises administering to the subject an effective amount of a compound of the present invention.

BRIEF DESCRIPTION OF THE FIGURE

The Figure is a schematic showing the synthesis of amonafide malate salt by the method disclosed herein. Many other organic carboxylic acid salts of the amonafide structural skeleton can be prepared by the method disclosed herein.

DETAILED DESCRIPTION OF THE INVENTION

The present invention is directed to organic carboxylic acid salts of amonafide and organic carboxylic acid salts of amonafide derivatives and precursors represented by Structural Formula (I). Preferably in Structural Formula (I), n is 2; R3 and R4 are the same and are —H, —CH$_3$ or —CH$_2$CH$_3$; and R2 is —NO$_2$, —NH$_2$ or —NH$_3$$^+$X$^-$. More preferably, n is 2; R3 and R4 are —CH$_3$; and R2 is —NO$_2$, —NH$_2$ or —NH$_3$$^+$X$^-$. Suitable values for X$^-$ are provided below.

The present invention is also directed to methods of preparing organic acid salts of amonafide and derivatives represented by Structural Formula (II) by hydrogenating compounds represented by Structural Formula (III) in water. Preferably in Structural Formula (II) and (III), n is 2; R3 and R4 are the same and are —H, —CH$_3$ or —CH$_2$CH$_3$. More preferably, n is 2; and R3 and R4 are —CH$_3$. Suitable values for X$^-$ are provided below.

Most preferably, the present invention is directed to organic carboxylic acid salts of amonafide and methods of preparation therefor. The structure of amonafide is represented by Structural Formula (IV):

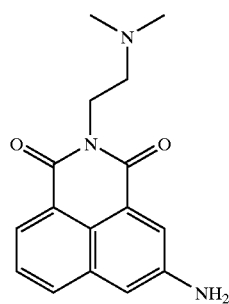
(IV).

The compounds disclosed herein with two amine groups, including amonafide salts, can be monovalent, meaning that one of the amine groups is protonated, or divalent, meaning that both amine groups are protonated. A divalent compound can be protonated by two different monocarboxylic acid compounds (i.e., the two Xs in Structural Formula (I) represent two different monocarboxylic acid compounds), by two molar equivalents of the same monocarboxylic acid compound (i.e., the two Xs in Structural Formula (I) each represent one molar equivalent of the same monocarboxylic acid compound), or by one molar equivalent of a dicarboxylic acid compound (i.e., the two Xs in Structural Formula (I) together represent one dicarboxylic acid compound). Alternatively, three molar equivalents a divalent compound are protonated by two molar equivalents of a tricarboxylic acid compound. All of these possibilities are meant to be included within Structural Formulas (I) and (IV) above.

An organic carboxylic acid compound is an organic compound having one or more carbon atoms and a carboxylic acid functional group. Suitable organic carboxylic acid compounds for use in preparing the compounds of the present invention are water soluble (typically a water solubility greater than 20% weight to volume), produce water soluble salts with aryl amines and alkyl amines and have a pKa>2.0. Included are aryl carboxylic acids, aliphatic carboxylic acids (typically C1–C4), aliphatic dicarboxylic acids (typically C2–C6), aliphatic tricarboxylic acids (typically C3–C8) and heteroalkyl carboxylic acids. An aliphatic carboxylic acid can be completely saturated (an alkyl carboxylic acid) or can have one or more units of unsaturation. A heteroalkyl carboxylic acid compound is an aliphatic carboxylic acid compound in which one or more methylene or methane groups are replaced by a heteroatom such as O, S, or NH. Examples of heteroalkyl carboxylic acid compounds include a C1–C5 heteroalkyl monocarboxylic acid compound (i.e., a C2–C6 alkyl monocarboxylic acid compound in which one methylene or methane group has been replaced with O, S or NH) and C3–C8 a heteroalkyl dicarboxylic acid compound (i.e., a C2–C7 alkyl dicarboxylic acid compound in which one methylene or methane group has been replaced with O, S or NH).

An aliphatic carboxylic acid compound can be straight or branched. An aliphatic carboxylic acid can be substituted (functionalized) with, one or more functional groups. Examples include a hydroxyl group (e.g., a hydroxy C2–C6 aliphatic monocarboxylic acids, a hydroxy C3–C8 aliphatic dicarboxylic acid and a hydroxy C4–C10 hydroxy aliphatic tricarboxylic acid), an amine (e.g., an amino C2–C6 aliphatic monocarboxylic acid, an amino C3–C8 aliphatic dicarboxylic acid and an amino C4–C10 aliphatic tricarboxylic acid), a ketone (e.g., a keto C2–C6 aliphatic monocarboxylic acid, a keto C3–C8 dicarboxylic acid or a keto C4–C10 tricarboxylic acid) or other suitable functional group.

Examples of Suitable Organic Acids are:

saturated aliphatic monocarboxylic acids such as formic acid, acetic acid or propionic acid;

unsaturated aliphatic monocarboxylic acids such as 2-pentenoic acid, 3-pentenoic acid, 3-methyl-2-butenoic acid or 4-methyl-3-pentenoic acid;

functionalized acids such as hydroxycarboxylic acids (e.g. lactic acid, glycolic, pyruvic acid, mandelic acid);

ketocarboxylic acids (e.g. oxaloacetic acid and alpha-ketoglutaric acid);

amino carboxylic acids (e.g. aspartic acid and glutamic acid);

saturated aliphatic dicarboxylic acids such as malonic acid, succinic acid or adipic acid;

unsaturated aliphatic dicarboxylic acids such as maleic acid or fumaric acid;

functionalized di- and tricarboxylic acids such as malic acid, tartaric acid, citric acid gluconic acid.

aryl carboxylic acids having sufficient water solubility, e.g., e.g., 4-hydroxybenzoic acid, salicylic acid, anthranilic acid, anisic acid and vanillic acid.

Non-aromatic nitrogen-containing heterocyclic rings are non-aromatic nitrogen-containing rings which include zero, one or more additional heteroatoms such as nitrogen, oxygen or sulfur in the ring. The ring can be five, six, seven or eight-membered. Examples include morpholinyl, thiomorpholinyl, pyrrolidinyl, piperazinyl, piperidinyl, azetidinyl, azacycloheptyl, or N-phenylpiperazinyl.

Hydrogenation of compounds represented by Structural Formula (III) is carried out under a hydrogen atmosphere at pressures between 5 and 50 pounds per square inch (psi), preferably between 13 and 17 psi. A hydrogenation catalyst is required, for example Pd/C, Pt/C, PtO$_2$, Raney Nickel and activated elemental iron or zinc. After hydrogenation, a monovalent compound is obtained. The corresponding divalent compound can be obtained by reacting the product with an additional equivalent of the same or different carboxylic acid compound.

The starting compound represented by Structural Formula (III) can be prepared by reacting the corresponding free base, i.e., where R1 is —(CH$_2$)$_n$NR3R4, with an organic carboxylic acid compound. Preferably, the resulting product is crystallized before hydrogenating. The free base can be prepared by reacting H$_2$N(CH$_2$)$_n$NR3R4 with 3-nitro-1,8-nitronaphthalic anhydride, wherein n, R3 and R4 are as defined in Structural Formula (I). Specific conditions for carrying out this reaction are described in U.S. Pat. No. 4,204,063, the entire teachings of which are incorporated herein by reference.

The compounds disclosed herein are useful for the treatment of cancer (e.g., leukemia and breast cancer) in a subject. A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

An "effective amount" is the quantity of compound in which a beneficial clinical outcome is achieved when the compound is administered to a subject with a multi-drug resistant cancer. A "beneficial clinical outcome" includes a reduction in tumor mass, a reduction in the rate of tumor growth, a reduction in metastasis, a reduction in the severity of the symptoms associated with the cancer and/or an increase in the longevity of the subject compared with the absence of the treatment. The precise amount of compound administered to a subject will depend on the type and severity of the disease or condition and on the characteristics of the subject, such as general health, age, sex, body weight and tolerance to drugs. It will also depend on the degree, severity and type of cancer. The skilled artisan will be able to determine appropriate dosages depending on these and other factors. Effective amounts of the disclosed compounds for therapeutic application typically range between about 0.35 millimoles per square meter of body surface area (mmole/msq) per day and about 2.25 millimoles per square meter of body surface area (mmole/msq) per day, and preferably between 1 mmole/msq and 1.5 mmole/msq on five day cycles by intravenous infusion.

The disclosed compounds are administered by any suitable route, including, for example, orally in capsules, suspensions or tablets or by parenteral administration. Parenteral administration can include, for example, systemic administration, such as by intramuscular, intravenous, subcutaneous, or intraperitoneal injection. The compounds can also be administered orally (e.g., dietary), topically, by inhalation (e.g., intrabronchial, intranasal, oral inhalation or intranasal drops), or rectally, depending on the type of cancer to be treated. Oral or parenteral administration are preferred modes of administration.

The disclosed compounds can be administered to the subject in conjunction with an acceptable pharmaceutical carrier as part of a pharmaceutical composition for treatment of cancer. Formulation of the compound to be administered will vary according to the route of administration selected (e.g., solution, emulsion, capsule). Suitable pharmaceutical carriers may contain inert ingredients which do not interact with the compound. Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextrasn) are known in the art (Baker, et al., "Controlled Release of Biological Active Agents", John Wiley and Sons, 1986).

EXEMPLIFICATION

The method of the invention is illustrated in more detail by the following examples which are not intended to be limiting in any way. The course of the organic acid salt formation of amonafide and analogs thereof can be followed via the determination of the products formed by means of chromatography and NMR spectroscopy. The formed salts are further characterized by mass spectrometry and by elementary analysis.

Example 1

Direct Synthesis of Intercalator Drug (Amonafide) as an Oragnic Acid (L-Malate) Salt The following synthetic scheme is meant to describe in detail the reaction shown in the Figure.

Preparation of Mitonafide Malate (III, FW 447.42)
Reactants:
(I) 3-nitro-1,8-nitronaphthalic anhydride, (FW 243.18, CAS 3027-38-1, purity 99%, ACROS, cat. #27873-0250);
(II) N,N-dimethylethylenediamine (FW 88.15, CAS 108-00-9, purity 99%,
    L-malic acid (FW 134.09, CAS 97-67-6, purity 99% ACROS cat. #15059-1000
Synthetic Procedure:

100 gr. (0.41 mol, 1 eq.) of the anhydride (I) were combined with 1300 ml of anhydrous ethanol in a 3L 3-neck round bottom flask fitted with an adding funnel and mechanical paddle stirrer. While vigorously stirring the suspension, a solution of 40 gr (0.45 mol, 1.1 eq.) of the diamine (II) in 100 ml of anhydrous ethanol was added as a rapid drip. Stirring was continued for 12 hours (overnight), and thereafter the mixture was brought to reflux for 1 hour.

Upon cooling to an internal temperature of 80° C., a pre-warmed (also to 80° C.) solution of 60 gr. (0.42 mol, 1.09 eq.) of L-malic acid in 100 ml of ethanol was added in one portion to the reaction flask and stirring continued for 3 hours. Stirring was stopped and when the reaction reaches room temperature, the crude mitonafide malate was recovered by filtration. The solids were resuspended in 1 liter of anhydrous isopropanol, refiltered, and rinsed with diethyl ether. They were then transferred to a drying dish, triturated mechanically and vacuum desiccated in a drying oven at 0.1 Torr with heating to 30° C. for 12 hours.

A tan solid (160 gr., 87% yield) was obtained, mp 160–162° C., homogenous by HPLC, under the conditions shown in Table 1, with a proton NMR spectrum (in perdeuterated acetic acid, 80 MHz) conforming to theory: malate-$CH_2$, 2.8 ppm, asymmetric doublet, 2H; N,N-$(CH_3)_2$, 3.1 ppm, singlet, 6H; imido-N—$CH_2$, 3.7 ppm, degenerate triplet, 2H; amino-N—$CH_2$ and malate-CH, 4.6 ppm, multiplet, 3H; aryl-CH, 8–9.3 ppm, two apparent triplets and doublet, 5H; OH, 11.4 ppm, singlet, 3H.

Recrystallization was achieved by suspending the product in aqueous ethanol (water/ethanol 1/5 v/v per gram of III), heating to boil and removing any insolubles by hot filtration. Upon cooling, the mass was filtered, rinsed with diethyl ether and vacuum desiccated to afford light tan, birefringent plates (140 gr, 76% overall yield), mp 163–164° C.

Preparation of Amonafide Malate (IV, FW 417.42)
Synthetic Procedure:

A solution of 134 gr. (0.3 mole) mitonafide malate (III) was suspended in 1 liter of deionized, degassed water under an argon blanket in a Parr hydrogenation pressure bottle. 1.4 gr. of 10% Pd/C are added, and the mixture was then evacuated and purged with hydrogen gas (three times), then connected to a Parr apparatus and pressurized with hydrogen gas to 15 psi. The reaction was vigorously shaken at room temperature becoming a yellow solution instead of a tan colored suspension within two hours. It was left to hydrogenate for an additional 12 hours (overnight).

After evacuative removal of the hydrogen headspace and replacement with nitrogen, the reaction mixture was stirred with 40 gr. of activated carbon, warmed to 50° C., and passed in a Buchner funnel through filter paper overlayed with pre-washed Celite filtration aid. The filtrate was concentrated in a 2 liter round bottom flask, under reduced pressure in a rotary evaporator with a heating bath thermostated to 50° C. When a thin crust had begun to form along the meniscus of the syrupy concentrate, which weighed between 240–250 gr, the flask was refrigerated (4° C.) for 12 hrs (overnight) to permit crystallization.

The resulting mustard yellow crystals and mother liquor were triturated with isopropanol, which was added in portions to a total volume of 1 liter. After an additional 2 hrs. of refrigeration, the suspension was filtered, washed with isopropanol and diethyl ether to afford IV, 113 gr. (90%), as a mustard yellow powder, mp 182–184° C., after desiccation in a heated vacuum oven (40–50° C., 0.5 Torr, 14 hrs.). The material was homogenous by HPLC, under the conditions shown in Table 1, with a proton NMR spectrum (in perdeuterated acetic acid, 80 MHz) conforming to theory: malate-$CH_2$, 2.8 ppm, asymmetric doublet, 2H; N,N-$(CH_3)_2$, 3.1 ppm, singlet, 6H; imido-N—$CH_2$, 3.7 ppm, degenerated triplet, 2H; amino-N—$CH_2$ and malate-CH, 4.6 ppm, multiplet, 3H; aryl-CH, 7.4–8.2 ppm, two apparent multiplets, 5H; OH, 11.4 ppm, singlet, 5H.

Recrystallization was achieved by dissolving the product in water (1/4 w/v per gr. of IV) and admixing with a hot mixture of 1/1 isopropanol/methanol (1/6 w/v per gr. of IV), heating to boil and removing any insolubles by hot filtration. Upon cooling first to room temperature and then upon chilling for 12 hrs. (0–4° C.), the mass was filtered, rinsed with isopropanol followed by diethyl ether and vacuum desiccated to afford 90 gr. of mustard yellow, rhomboid crystals (85 gr., 68% overall yield), mp 184–185° C.

TABLE 1

HPLC OF MITONAFIDE AND AMONAFIDE MALATE

| Column* | Mobile Phase** | Flow Rate ml/min | Col Temp (C.°) | Rt AMFm | Rt MiTm |
|---|---|---|---|---|---|
| Nova Pak C18 | | | | | |
| 4 um 60A° | 17/55/28 | 1.0 | 30 | >30 | NA |
| 3.9 × 150 mm. | 30/35/35 | 2.5 | 40 | 10.2 | 13.2 |
|  | 40/25/35 | 2.5 | 40 | 5.1 | 4.7 |
| Xterra MS C18 | 17/55/28 | 0.8 | 40 | 1.4 | 3.1 |
| 3.5 uM | 17/55/28 | 0.8 | 30 | 2.3 | NA |
| 3.0 × 150 mm. | | | | | |

*End-capped (shielded) columns should be used
**$CH_3CN$, $H_2O$, MeOH v/v/v
AMFm = amonafide malate
MiTn = mitonafide malate

Example 2

Synthesis of Amonafide Organic Carboxylic Acid Salts by Titration

The method of Example 2, illustrating the total synthesis of amonafide by a sequence of steps in which the organic acid is incorporated at the outset, can be extended to the use of organic acids other than L-malate. These can be incorporated at any stage in the synthesis scheme, where appropriate to the reaction flow and consistent with sound chemical practice. By way of convenient illustration, a panel of salts were readily prepared in semi-automated fashion. It should be understood that any analog or congener thereof, with similar aralkylamine derived basicity properties, would be equally suitable as an exemplar.

First a stock solution of amonafide, was dispensed into individual reaction vials so as to provide a defined amount of basic substrate. It was then titrated with a second solution containing one stoichiometric equivalent of an appropriate organic carboxylic acid, whose acidity is consistent with an aqueous pKa value of not less than 3. The resulting mixture was warmed in order to effect complete dissolution and neutralization of the species reacting ionically, and allowed to deposit the resulting salts as products upon cooling. These solutions may also be concentrated, prior to cooling, in order to optimize the reaction yield. However, for optimal results the reaction solvent in this manipulation should be selected so that the reactants are individually more soluble than their ionic combination.

In an illustrative example, the free base material was synthesized according to Brana et al in U.S. Pat. No. 5,183,821. An aliquot was dissolved in boiling anhydrous ethanol at a concentration of 1 gram per 20 ml. 10 ml of solution prepared in this manner contains 1.765 mMol of material and would, therefore, become neutralized by an equivalent amount of an appropriate organic carboxylic acid in order to afford a monovalent organic salt. Since amonafide is divalent, in theory, it can also be titrated with two equivalents of organic acid to afford a divalent salt. Thus, the number of acid equivalents that can be added should at least match the calculated minimum number of basic equivalents in the intercalator free drug and not exceed the maximum such number.

For the purpose of this example, however, salt formation has been restricted to monoequivalents, and, therefore, solutions of organic carboxylic acids containing 1.765 mMol in 10–20 ml of water at boil were prepared and added individually to each of several replicate 100 ml portions of the drug free base at the concentration and volume just described. After bringing the mixed solutions again up to boil, to insure complete dissolution of all ingredients, they were then left to cool at room temperature and refrigerated overnight, whereupon the resulting crystalline salts were harvested by filtration, dried by rinsing with diethyl ether, and desiccated under vacuum.

Table 2 provides a listing of the organic carboxylic acids that were used to titrate amonafide in order to produce the corresponding crystalline monovalent salt. Salts obtained in this manner may be characterized variously by chromatography for chemical homogeneity, and by NMR or mass spectrometry for purposes of structural characterization, as described herein above in Example 1. Characterization by elemental composition also affords a convenient method for identity verification. As shown in Table 2, the observed compositions in Part I and the theoretical elemental compositions in Part II are closely matched, demonstrating that the reaction products constitute an equimolar addition of each reactant, as would be anticipated for any such monovalent adducts of an organic base and an organic acid.

TABLE 2

AMONAFIDE SALTS

COMPOSITION OF ORGANIC SALT

| Acid | C | H | N | O |
|---|---|---|---|---|
| Part I | Observed | | | |
| A) succinic | 59.54 | 5.89 | 10.13 | 24.44 |
| B) maleic | 60.37 | 5.10 | 10.23 | 24.30 |
| C) fumaric | 59.89 | 5.52 | 10.20 | 24.39 |
| D) citric | 54.87 | 5.78 | 8.30 | 31.05 |
| E) L-tartaric | 56.27 | 4.95 | 9.23 | 29.55 |
| F) L-aspartic | 56.80 | 6.02 | 13.78 | 23.40 |
| G) pyruvic | 62.45 | 5.34 | 11.00 | 21.21 |
| H 2-oxoglutaric | 58.12 | 5.30 | 10.40 | 26.18 |

TABLE 2-continued

AMONAFIDE SALTS

COMPOSITION OF ORGANIC SALT

| Acid | C | H | N | O |
|---|---|---|---|---|
| Part II | Calculated | | | |
| A) succinic | 59.84 | 5.78 | 10.47 | 23.91 |
| B) maleic | 60.14 | 5.30 | 10.52 | 24.03 |
| C) fumaric | 60.14 | 5.30 | 10.52 | 24.03 |
| D) citric | 55.58 | 5.30 | 8.84 | 30.29 |
| E) L-tartaric | 55.42 | 5.35 | 9.69 | 29.53 |
| F) L-aspartic | 57.69 | 5.81 | 13.45 | 23.05 |
| G) pyruvic | 61.45 | 5.70 | 11.31 | 21.54 |
| H 2-oxoglutaric | 58.74 | 5.40 | 9.79 | 26.08 |

Further confirmation of structural identity and purity was also obtained in each instance by NMR analysis in perdeutero acetic acid, the salt of amonafide and succinic acid being representative, in so far as it is a comparable analog to the malate salt prepared in Example 1. Thus, the salt shown prepared according to Table 2, Part I, entry A, as the monoequivalent combination of amonafide and succinic acid showed a proton NMR spectrum (in perdeuterated acetic acid, 80 MHz) conforming to theory: succinate-$CH_2$, 2.7 ppm, singlet, 6H; N,N-$(CH_3)_2$, 3.1 ppm, singlet, 6H; imido-N—$CH_2$, 3.7 ppm, degenerated triplet, 2H; amino-N—$CH_2$, 4.6 ppm, degenerated triplet, 2H; aryl-CH, 7.4–8.3 ppm, two apparent multiplets, 5H; OH, 11.4 ppm, singlet, 4H.

Although this example illustrates the use of several chiral molecules, as for example in entries E-F, it follows that suitable results for purposes of salt formation can be obtained with the corresponding racemic form or alternate antipodes of such acids. Thus, the selection of the L-enantiomers in this instance should not be taken as a restriction of the teaching; but, rather, as a case in point that would be understood by those practiced in the art to be the most commonly available such organic carboxylic acid forms suitable for purposes of biological experimentation.

While this invention has been particularly shown and described with references to preferred embodiments thereof, it will be understood by those skilled in the art that various changes in form and details may be made therein without departing from the scope of the invention encompassed by the appended claims.

What is claimed is:
1. Amonafide malate.
2. Monovalent amonafide malate.
3. A method of preparing a product compound represented by the following structural formula:

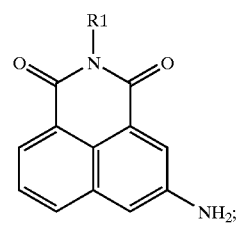

from a starting compound represented by the following structural formula:

[Structural formula: 1,8-naphthalimide with R1 on N and NO2 substituent]

wherein:
R1 is —(CH$_2$)$_n$N$^+$HR3R4 X$^-$;
R3 and R4 are independently H, C1–C4 alkyl group or, taken together with the nitrogen atom to which they are bonded, a non-aromatic nitrogen-containing heterocyclic group;
n is an integer from 0–3; and
X$^-$ is the carboxylate anion of an organic carboxylic acid compound,
said method comprising the step of hydrogenating the starting compound in water, thereby forming the product compound.

4. The method of claim 3 wherein:
n is 2; and
R3 and R4 are the same and are —H, —CH$_3$ or —CH$_2$CH$_3$.

5. The method of claim 4 wherein R3 and R4 are —CH$_3$.

6. The method of claim 3 wherein X$^-$ is the carboxylate anion of a C1–C4 aliphatic monocarboxylic acid, hydroxy C2–C6 aliphatic monocarboxylic acid, keto C2–C6 aliphatic monocarboxylic acid, amino C2–C6 aliphatic monocarboxylic acid, C2–C8 aliphatic dicarboxylic acid, hydroxy C3–C8 aliphatic dicarboxylic acid, keto C3–C8 aliphatic dicarboxylic acid, amino C3–C8 aliphatic dicarboxylic acid, C3–C8 aliphatic tricarboxylic acid, hydroxy C4–C10 tricarboxylic acid, keto C4–C10 tricarboxylic acid, amino C4–C10 tricarboxylic acid, an aryl carboxylic acid, C1–C5 heteroalkyl monocarboxylic acid or C3–C8 heteroalkyl dicarboxylic acid.

7. The method of claim 5 wherein X$^-$ is the carboxylate anion of a C1–C4 aliphatic monocarboxylic acid, hydroxy C2–C6 aliphatic monocarboxylic acid, keto C2–C6 aliphatic monocarboxylic acid, amino C2–C6 aliphatic monocarboxylic acid, C2–C8 aliphatic dicarboxylic acid, hydroxy C3–C8 aliphatic dicarboxylic acid, keto C3–C8 aliphatic dicarboxylic acid, amino C3–C8 aliphatic dicarboxylic acid, C3–C8 aliphatic tricarboxylic acid, hydroxy C4–C10 tricarboxylic acid, keto C4–C10 tricarboxylic acid, amino C4–C10 tricarboxylic acid, an aryl carboxylic acid, C1–C5 heteroalkyl monocarboxylic acid or C3–C8 heteroalkyl dicarboxylic acid.

8. The method of claim 3 wherein X$^-$ is the carboxylate anion of formic acid, acetic acid, propionic acid, 2-pentenoic acid, 3-pentenoic acid, 3-methyl-2-butenoic acid, 4-methyl-3-pentenoic acid, lactic acid, glycolic, mandelic acid, oxaloacetic acid, alpha-ketoglutaric acid, aspartic acid, glutamic acid, malonic acid, succinic acid, adipic acid, maleic acid, fumaric acid, malic acid, tartaric acid, citric acid or gluconic acid.

9. The method of claim 5 wherein X$^-$ is the carboxylate anion of formic acid, acetic acid, propionic acid, 2-pentenoic acid, 3-pentenoic acid, 3-methyl-2-butenoic acid, 4-methyl-3-pentenoic acid, lactic acid, glycolic, mandelic acid, oxaloacetic acid, alpha-ketoglutaric acid, aspartic acid, glutamic acid, malonic acid, succinic acid, adipic acid, maleic acid, fumaric acid, malic acid, tartaric acid, citric acid or gluconic acid.

10. The method of claim 3 wherein X$^-$ is malate.
11. The method of claim 5 wherein X$^-$ is malate.
12. The method of claim 3 wherein the starting compound is prepared by reacting HX with a precursor compound represented by the following structural formula:

[Structural formula: 1,8-naphthalimide with R10 on N and NO2 substituent]

wherein R10 is —(CH$_2$)$_n$NR3R4.

13. The method of claim 12 wherein n is 2 and R3 and R4 are both methyl.

14. The method of claim 12 wherein HX is a C1–C4 aliphatic monocarboxylic acid, hydroxy C2–C6 aliphatic monocarboxylic acid, keto C2–C6 aliphatic monocarboxylic acid, amino C2–C6 aliphatic monocarboxylic acid, C2–C8 aliphatic dicarboxylic acid, hydroxy C3–C8 aliphatic dicarboxylic acid, keto C3–C8 aliphatic dicarboxylic acid, amino C3–C8 aliphatic dicarboxylic acid, C3–C8 aliphatic tricarboxylic acid, hydroxy C4–C10 tricarboxylic acid, keto C4–C10 tricarboxylic acid, amino C4–C10 tricarboxylic acid, an aryl carboxylic acid, C1–C5 heteroalkyl monocarboxylic acid or C3–C8 heteroalkyl dicarboxylic acid.

15. The method of claim 13 wherein HX is a C1–C4 aliphatic monocarboxylic acid, hydroxy C2–C6 aliphatic monocarboxylic acid, keto C2–C6 aliphatic monocarboxylic acid, amino C2–C6 aliphatic monocarboxylic acid, C2–C8 aliphatic dicarboxylic acid, hydroxy C3–C8 aliphatic dicarboxylic acid, keto C3–C8 aliphatic dicarboxylic acid, amino C3–C8 aliphatic dicarboxylic acid, C3–C8 aliphatic tricarboxylic acid, hydroxy C4–C10 tricarboxylic acid, keto C4–C10 tricarboxylic acid, amino C4–C10 tricarboxylic acid, an aryl carboxylic acid, C1–C5 heteroalkyl monocarboxylic acid or C3–C8 heteroalkyl dicarboxylic acid.

16. The method of claim 12 wherein HX is formic acid, acetic acid, propionic acid, 2-pentenoic acid, 3-pentenoic acid, 3-methyl-2-butenoic acid, 4-methyl-3-pentenoic acid, lactic acid, glycolic, mandelic acid, oxaloacetic acid, alpha-ketoglutaric acid, pyruvic acid, aspartic acid, glutamic acid, malonic acid, succinic acid, adipic acid, maleic acid, fumaric acid, malic acid, tartaric acid, citric acid or gluconic acid.

17. The method of claim 13 wherein HX is formic acid, acetic acid, propionic acid, 2-pentenoic acid, 3-pentenoic acid, 3-methyl-2-butenoic acid, 4-methyl-3-pentenoic acid, lactic acid, glycolic, mandelic acid, oxaloacetic acid, alpha-ketoglutaric acid, pyruvic acid, aspartic acid, glutamic acid, malonic acid, succinic acid, adipic acid, maleic acid, fumaric acid, malic acid, tartaric acid, citric acid or gluconic acid.

18. The method of claim 12 wherein HX is malic acid.
19. The method of claim 13 wherein HX is malic acid.
20. The method of claim 3 wherein the starting compound is crystallized before hydrogenating.
21. The method of claim 5 wherein the starting compound is crystallized before hydrogenating.
22. The method of claim 12 wherein the precursor compound is prepared by reacting 3-nitro-1,8-nitrophthalic anhydride with H$_2$N—(CH$_2$)$_n$NR3R4.
23. The method of claim 12 wherein the precursor compound is prepared by reacting 3-nitro-1,8-nitrophthalic anhydride with H$_2$N—(CH$_2$)$_2$N(CH$_3$)$_2$.
24. A method of preparing an organic carboxylic acid salt of amonafide comprising the steps of:

a) reacting 3-nitro-1,8-nitrophthalic anhydride with H$_2$N—(CH$_2$)$_2$N(CH$_3$)$_2$ to form mitonafide;

b) reacting mitonafide with an organic carboxylic acid compound to form an organic carboxylic acid salt of mitonafide;

c) crystallizing the organic carboxylic acid salt of mitonafide; and d) hydrogenating in water the crystallized organic carboxylic acid salt of mitonafide to form the organic carboxylic acid salt of amonafide.

25. The method of claim 24 wherein the organic carboxylic acid is formic acid, acetic acid, propionic acid, 2-pentenoic acid, 3-pentenoic acid, 3-methyl-2-butenoic acid, 4-methyl-3-pentenoic acid, lactic acid, glycolic, mandelic acid, oxaloacetic acid, alpha-ketoglutaric acid, aspartic acid, glutamic acid, malonic acid, succinic acid, adipic acid, maleic acid, fumaric acid, malic acid, tartaric acid, citric acid or gluconic acid.

26. A method of preparing a malic acid salt of amonafide comprising the steps of:

a) reacting 3-nitro-1,8-nitrophthalic anhydride with H$_2$N—(CH$_2$)$_2$N(CH$_3$)$_2$ to form mitonafide;

b) reacting mitonafide with a malic acid to form a malic acid salt of mitonafide;

c) crystallizing the malic acid salt of mitonafide; and d) hydrogenating in water the crystallized malic acid salt of mitonafide to form the malic acid salt of amonafide.

27. Amonafide-glycolate.

* * * * *